US011173047B2

(12) United States Patent
Milz et al.

(10) Patent No.: US 11,173,047 B2
(45) Date of Patent: Nov. 16, 2021

(54) SURGICAL INSTRUMENT WITH ANGLED DRIVE SHAFT

(71) Applicant: Stryker European Operations Holdings LLC, Kalamazoo, MI (US)

(72) Inventors: Bryan D. Milz, Florida, NY (US); Zinoviy Sosnov, Fair Lawn, NJ (US); Brian Haight, Sussex, NJ (US); Frank Pinal, Jersey City, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 255 days.

(21) Appl. No.: 16/434,572

(22) Filed: Jun. 7, 2019

(65) Prior Publication Data
US 2019/0374350 A1 Dec. 12, 2019

Related U.S. Application Data

(60) Provisional application No. 62/681,946, filed on Jun. 7, 2018.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4465* (2013.01); *A61F 2002/30133* (2013.01);
(Continued)

(58) Field of Classification Search
CPC ........ A61F 2/44; A61F 2/4455; A61F 2/4465; A61F 2/46; A61F 2/4603; A61F 2/4611;
(Continued)

(56) References Cited

U.S. PATENT DOCUMENTS

| 6,004,326 A | 12/1999 | Castro et al. |
| 6,095,020 A * | 8/2000 | Rinner .................... B25B 15/02 |
| | | 81/475 |

(Continued)

FOREIGN PATENT DOCUMENTS

| FR | 2923153 A1 | 5/2009 |
| WO | 9531948 A1 | 11/1995 |

(Continued)

OTHER PUBLICATIONS

Stryker, AccuLIF, Expandable TLIF and PLIF Technology, Surgical Technique Guide, Copyright 2015, pp. 1-48.

(Continued)

*Primary Examiner* — Eric S Gibson
(74) *Attorney, Agent, or Firm* — Lerner, David, Littenberg, Krumholz & Mentlik, LLP

(57) ABSTRACT

A surgical instrument includes a body having a proximal end and a distal end and defining a lumen extending from the proximal end to the distal end along an axis, the distal end configured to abut an implant, and an anchor rod disposable within the lumen of the body for contacting the implant to secure the implant at the distal end of the body. When the anchor rod is disposed within the lumen of the body in a working configuration, the anchor rod is connected to the body at the proximal end of the body and at the distal end of the body to substantially fix the anchor rod from moving along the axis of the lumen. The body includes a handle, a shaft extending distally from the handle, and a torque limiting mechanism.

20 Claims, 19 Drawing Sheets

(52) U.S. Cl.
CPC .............. *A61F 2002/30622* (2013.01); *A61F 2002/4629* (2013.01)

(58) Field of Classification Search
CPC ...... A61F 2002/4625; A61F 2002/4627; A61F 2002/4629; A61F 2002/4666; A61F 2002/4667
See application file for complete search history.

(56) References Cited

U.S. PATENT DOCUMENTS

| | | | |
|---|---|---|---|
| 6,830,574 B2 | 12/2004 | Heckele et al. | |
| 7,235,082 B2 | 6/2007 | Bartish et al. | |
| 7,334,509 B1 * | 2/2008 | Gao | B25B 15/02 |
| | | | 81/467 |
| 7,575,580 B2 | 8/2009 | Lim et al. | |
| 7,892,239 B2 * | 2/2011 | Warnick | A61F 2/4611 |
| | | | 606/99 |
| 7,976,549 B2 | 7/2011 | Dye et al. | |
| 7,988,695 B2 * | 8/2011 | Dye | A61F 2/4611 |
| | | | 606/86 A |
| 8,147,554 B2 | 4/2012 | Hansell et al. | |
| 8,241,364 B2 | 8/2012 | Hansell et al. | |
| 8,252,060 B2 * | 8/2012 | Hansell | A61F 2/4611 |
| | | | 623/17.16 |
| 8,343,224 B2 * | 1/2013 | Lynn | A61F 2/4601 |
| | | | 623/17.16 |
| 8,992,620 B2 | 3/2015 | Ashley et al. | |
| 8,998,924 B2 * | 4/2015 | Simpson | A61F 2/4611 |
| | | | 606/105 |
| 9,095,385 B2 * | 8/2015 | Wallenstein | A61F 2/4611 |
| 9,445,918 B1 * | 9/2016 | Lin | A61B 17/8819 |
| 9,668,876 B2 | 6/2017 | Blain et al. | |
| 9,681,961 B2 | 6/2017 | Prevost et al. | |
| 9,987,149 B2 * | 6/2018 | Simpson | A61F 2/4611 |
| 2006/0155297 A1 | 7/2006 | Ainsworth et al. | |
| 2006/0235426 A1 * | 10/2006 | Lim | A61F 2/4611 |
| | | | 606/99 |
| 2007/0093850 A1 * | 4/2007 | Harris | H05B 47/11 |
| | | | 606/99 |
| 2007/0093897 A1 | 4/2007 | Gerbec et al. | |
| 2007/0225726 A1 * | 9/2007 | Dye | A61F 2/4465 |
| | | | 606/99 |
| 2008/0065082 A1 * | 3/2008 | Chang | A61B 17/1671 |
| | | | 606/85 |
| 2008/0077150 A1 | 3/2008 | Nguyen | |
| 2008/0091211 A1 * | 4/2008 | Gately | A61F 2/4611 |
| | | | 606/99 |
| 2008/0109005 A1 * | 5/2008 | Trudeau | A61F 2/442 |
| | | | 606/99 |
| 2008/0306489 A1 * | 12/2008 | Altarac | A61F 2/4611 |
| | | | 606/99 |
| 2008/0306557 A1 | 12/2008 | Altarac et al. | |
| 2010/0070035 A1 | 3/2010 | Mayer | |
| 2010/0249798 A1 * | 9/2010 | Sournac | A61B 17/7076 |
| | | | 606/104 |
| 2011/0130835 A1 | 6/2011 | Ashley et al. | |
| 2011/0276142 A1 * | 11/2011 | Niemiec | A61F 2/4425 |
| | | | 623/17.16 |
| 2012/0150241 A1 | 6/2012 | Ragab et al. | |
| 2012/0265304 A1 | 10/2012 | Mayer | |
| 2014/0142642 A1 * | 5/2014 | Wallenstein | A61B 17/7074 |
| | | | 606/86 A |
| 2015/0351925 A1 | 12/2015 | Emerick et al. | |
| 2016/0317324 A1 * | 11/2016 | Cho | A61F 2/4611 |
| 2017/0258605 A1 | 9/2017 | Blain et al. | |
| 2017/0290671 A1 | 10/2017 | Milz et al. | |
| 2017/0290680 A1 * | 10/2017 | Pinal | A61F 2/4455 |
| 2017/0319352 A1 | 11/2017 | Dewey et al. | |
| 2017/0333199 A1 | 11/2017 | Sharifi-Mehr et al. | |
| 2019/0374350 A1 * | 12/2019 | Milz | B25B 23/1427 |

FOREIGN PATENT DOCUMENTS

| | | |
|---|---|---|
| WO | 2002017823 A1 | 3/2002 |
| WO | 2008041972 A2 | 4/2008 |
| WO | 2011139905 A2 | 11/2011 |

OTHER PUBLICATIONS

Depuysynthes: "System Guide Expedium Verse Spinal System", Apr. 22, 2016 (Apr. 22, 2016), XP055630659, Retrieved from the Internet: URL:https://tehranarkak.net/files/DSEM-SPN-0915-0337-1_LR.pdf [retrieved on Oct. 10, 2019].

Dr Rudolf Morgenstern: "Concorde Lift (TM) Expandable Interbody Device Surgical Technique Utilizing technology developed by", Jul. 4, 2017 (Jul. 4, 2017), XP055630654, Retrieved from the Internet: RL:http://www.thespinemarketgroup.com/wp-content/uploads/2018/04/Surgical-Technique-Guide-CONCORDE-LIFT.pdf [retrieved on Oct. 10, 2019].

Extended European Search Report including the Written Opinion for Application No. EP 19178935.3 dated Oct. 17, 2019, 9 pages.

Innnovasis: "Ax (TM) Stand-Alone ALIF System",Apr. 18, 2017 (Apr. 18, 2017), XP055630652, Retrieved from the Internet: URL: https://static1.squarespace.com/static/5851914617eOab1 62532f8ff/ti58f92cf9414fb56b014ecc0c/1492725008405/L00063+Rev+D,+Ax+Surgical+ Technique+Guide.pdf [retrieved on Oct. 10, 2019].

* cited by examiner

SURGICAL INSTRUMENT WITH ANGLED DRIVE SHAFT

CROSS-REFERENCE TO RELATED APPLICATIONS

The present application claims the benefit of the filing date of U.S. Provisional Patent Application No. 62/681,946 filed Jun. 7, 2018, the disclosure of which is hereby incorporated herein by reference.

BACKGROUND OF THE INVENTION

The present inventions relate to surgical instruments used during the insertion of spinal implants and methods of using such instruments. More particularly, the present inventions relate to instruments including internal joints for articulation to provide greater control over spinal implant insertion from various positions and angles.

Intervertebral implants are commonly used in spinal surgery in which an implant (e.g., a spacer or cage) is placed in the disc space between two vertebrae to be fused together. One such type of application is an interbody fusion procedure. At least a portion of the disc is typically removed before the implant is positioned in the intervertebral space. The implant may be supplemented with bone graft material to promote fusion of the vertebrae. These procedures may also be performed in conjunction with other types of fixation, such as pedicle screw fixation, to provide additional stability, particularly while the vertebrae fuse together.

Interbody fusion procedures can be distinguished by the type of implant used, by their location along the spine (cervical, thoracic, or lumbar, for example), and by the surgical approach to the intervertebral space. Different surgical approaches may suggest or require the use of structural characteristics of the implant(s) used. Different surgical approaches to the spine include anterior, posterior, and lateral. Posterior lumbar interbody fusion (PLIF) and transforaminal lumbar interbody fusion (TLIF) are examples of interbody fusion techniques performed along a posterior approach. PLIF techniques typically include positioning two intervertebral implants into the intervertebral space along a posterior to anterior direction, with one implant being positioned towards the left side of the spine and one implant being positioned towards the right side of the spine. Implants used in such PLIF techniques typically have a straight shape extending along a central axis. On the other hand, TLIF techniques typically include positioning one intervertebral implant into the intervertebral space (often towards the anterior portion of the intervertebral space) from the posterior approach, but the spine is approached on one side from a more lateral position than in PLIF techniques. The implants used in such TLIF techniques are often curved in that they have an overall kidney bean-like shape.

When it is desired to insert an implant to a final position that is angled with respect to the axis of insertion, particularly in a TLIF procedure, specialized instruments are often useful in allowing final placement of the implant while maintaining a small surgical site. For example, angled instruments can permit access to more of the intervertebral disc space than a straight instrument may allow.

Further improvement is desired in the field of spinal implant instrumentation for devices that have increased functionality and durability for multiple uses.

BRIEF SUMMARY OF THE INVENTION

A first aspect of the present invention is a surgical instrument including a body having a proximal end and a distal end and defining a lumen extending from the proximal end to the distal end along an axis, the distal end being connectable with or configured to abut an implant, and an anchor rod disposable within the lumen of the body for contacting the implant to secure the implant at the distal end of the body, wherein when the anchor rod is disposed within the lumen of the body in a working configuration, the anchor rod is connected to the body at the proximal end and at the distal end of the body to substantially fix the anchor rod from moving along the axis of the lumen.

In accordance with other embodiments of the first aspect, when the anchor rod is in the working configuration, the anchor rod may be connected to the body at the proximal end by a proximal stop of the anchor rod in contact with a proximal stop of the body. When the anchor rod is in the working configuration, the anchor rod may be connected to the body at the proximal end by a proximally-facing surface of the anchor rod in contact with a distally-facing surface of the body. The proximal stop of the body may be located on a movable toggle. The toggle can be located in an unlocked position in which the proximal stop of the anchor rod can move distally past the proximal stop of the body, and in a locked position in which the proximal stop of the anchor rod contacts the proximal stop of the body and cannot move proximally past the proximal stop of the body. The toggle may be biased into the locked position. The toggle may be biased by a spring. The toggle may be temporarily moved to the unlocked position by contact with the anchor rod as the proximal stop of the anchor rod is moved distally past the proximal stop of the toggle. The proximal stop of the body may define a portion of an aperture of a lumen of the toggle.

The proximal stop of the anchor rod may be annular. When the anchor rod is in the working configuration, the annular proximal stop of the anchor rod may include a proximally-facing annular surface in contact with a distally-facing surface of the body. When the anchor rod is in the working configuration, the anchor rod may be connected to the body at the distal end by a distal stop of the anchor rod in contact with a distal stop of the body. When the anchor rod is in the working configuration, the anchor rod may be connected to the body at the distal end by a distally-facing surface of the anchor rod in contact with a proximally-facing surface of the body. The distal stop of the anchor rod may be annular. When the anchor rod is in the working configuration, the annular distal stop of the anchor rod may include a distally-facing annular surface in contact with a proximally-facing surface of the body. The distally-facing surface of the anchor rod and the proximally-facing surface of the body may both be annular surfaces. The anchor body may be comprised of a longitudinal shaft and a distal shaft that are translatable relative to one another along an anchor body axis. The longitudinal shaft and the distal shaft may be biased to move away from one another by an anchor body spring. When the anchor rod is in the working configuration, the anchor body spring may be at least partially compressed to exert force by the proximal stop of the anchor rod on the proximal stop of the body and by the distal stop of the anchor rod on the distal stop of the body.

When the anchor rod is in the working configuration, the anchor rod may be secured to the body at the proximal end and at the distal end of the body. The anchor body may be comprised of a longitudinal shaft and a distal shaft that are translatable relative to one another along an anchor body axis. The longitudinal shaft and the distal shaft may be biased to move away from one another by an anchor body spring. When the anchor rod is in the working configuration, the anchor body spring may be at least partially compressed to provide forces used to secure the anchor rod to the body at the proximal and distal ends of the body. The anchor body may be comprised of a longitudinal shaft and a distal shaft that are biased to translate away from one another along an anchor body axis by an anchor body spring, wherein the anchor body spring is at least partially compressed to provide forces used to secure the anchor rod to the body at the proximal and distal ends of the body. The body may define a joint permitting the distal end to articulate relative to the proximal end. The anchor rod may have a linkage connecting proximal and distal ends thereof, wherein the body and the anchor rod can articulate together when the anchor rod is disposed within the body and the joint and the linkage are aligned. A kit may include the surgical instrument as described herein, and a spinal implant.

The body may include a handle, a shaft extending distally from the handle, and a torque limiting mechanism. The torque limiting mechanism may be attached to a proximal end of the handle. The torque limiting mechanism may be in the handle. When the anchor rod is in the working configuration, the torque limiting mechanism may be connected with the anchor rod to cause rotation of the anchor rod about the axis of the lumen when a portion of the torque limiting mechanism is rotated about an axis of the torque limiting mechanism. The torque limiting mechanism may include a first gear mechanism defining a lumen in which a portion of the anchor rod is disposed when the anchor rod is in the working configuration, and a second gear mechanism connected to the first gear mechanism. The lumen of the first gear mechanism may have a non-circular cross section substantially matching a noncircular cross section of the portion of the anchor rod so that rotational forces of the first gear mechanism are transferred to rotational forces of the anchor rod. Rotation of the second gear mechanism in a first direction about the axis of the torque limiting mechanism may cause rotation of the first gear mechanism about the axis of the torque limiting mechanism up to a predetermined maximum torque value applied to the second gear mechanism, and rotation of the second gear mechanism in a second direction opposite the first direction about the axis of the torque limiting mechanism may always cause rotation of the first gear mechanism about the axis of the torque limiting mechanism. The first and second gear mechanisms may each have teeth that provide an interface, the interfaces engaging with one another to facilitate the transfer of torque from one of the first and second gear mechanisms to the other. The teeth of each of the first and second gear mechanisms may each be defined by a first tooth surface substantially parallel with the axis of the torque limiting mechanism and a second tooth surface angled with respect to the axis of the torque limiting mechanism. When the second gear mechanism is rotated in the first direction about the axis of the torque limiting mechanism, the second tooth surface of each of the teeth of the first and second gear mechanisms may be respectively engaged to transfer torque from the second gear mechanism to the first gear mechanism. When the predetermined maximum torque value is exceeded, rotation of the second gear mechanism may result in movement of the second gear mechanism with respect to the first gear mechanism about the axis of the torque limiting mechanism such that the interfaces of the first and second gear mechanisms disengage and no torque is transferred to the first gear mechanism. When the second gear mechanism is rotated in the second direction about the axis of the torque limiting mechanism, the first tooth surface of each of the teeth of the first and second gear mechanisms may be respectively engaged to transfer torque from the second gear mechanism to the first gear mechanism. The torque limiting mechanism may further include a spring that forces the teeth of the first and second gear mechanisms into engagement with each other when the torque limiting mechanism is at rest. The teeth of the first and second gear mechanisms may be forced into engagement with each other until the predetermined maximum torque value is exceeded.

A second aspect of the present invention is a surgical instrument including a body having a proximal end and a distal end and defining a lumen extending from the proximal end to the distal end along an axis, the distal end being connectable with or configured to abut an implant, and an anchor rod disposable within the lumen of the body for contacting the implant to secure the implant at the distal end of the body, wherein when the anchor rod is disposed within the lumen of the body in a working configuration, the body imposes a distally-facing force at the proximal end of the anchor rod and a proximally-facing force at the distal end of the anchor rod to substantially fix the anchor rod from movement along the axis of the lumen.

A third aspect of the present invention is a surgical instrument including a hollow body extending along an axis and having a proximal end and a distal end connectable with or configured to abut an implant, and an anchor rod movable within the hollow body along the axis for contacting the implant to secure the implant at the distal end of the body, wherein when the anchor rod is disposed within the hollow body in a working configuration, the body imposes a distally-facing force at the proximal end of the anchor rod and a proximally-facing force at the distal end of the anchor rod to substantially fix the anchor rod from movement along the axis.

A fourth aspect of the present invention is a surgical instrument including a body having a proximal end and a distal end and defining a lumen extending from the proximal end to the distal end along an axis, the distal end being connectable with or configured to abut an implant, and an anchor rod disposable within the lumen of the body for contacting the implant to secure the implant at the distal end of the body, wherein when the anchor rod is disposed within the lumen of the body in a working configuration, the anchor rod is captured by the body at the proximal end and at the distal end of the body to substantially fix the anchor rod from moving along the axis of the lumen.

A fifth aspect of the present invention is a surgical instrument including a body having a proximal end and a distal end and defining a lumen extending from the proximal end to the distal end along an axis, the distal end being connectable with or configured to abut an implant, and an anchor rod fixable within the lumen of the body for contacting the implant to secure the implant at the distal end of the body, wherein in a working configuration, the anchor rod is pinned within the body at the proximal end and at the distal end of the body to substantially fix the anchor rod from moving along the axis of the lumen.

A sixth aspect of the present invention is a surgical instrument including a body having a proximal end and a distal end and defining a lumen extending from the proximal end to the distal end along an axis, the distal end being connectable with or configured to abut an implant, and an anchor rod disposable within the lumen of the body for contacting the implant to secure the implant at the distal end of the body, wherein when the anchor rod is disposed within the lumen of the body in a working configuration, the anchor rod is connected to the body to substantially fix the anchor rod from moving along the axis of the lumen.

In accordance with other embodiments of the sixth aspect, the anchor rod may be connected to the body at two locations of the body. The two locations may be the proximal and distal ends of the body.

A seventh aspect of the present invention is a surgical instrument including a body having a proximal end and a distal end and defining a lumen extending from the proximal end to the distal end along an axis, the distal end being connectable with or configured to abut an implant, and an anchor rod disposable within the lumen of the body for contacting the implant to secure the implant at the distal end of the body, wherein the body comprises a handle, a shaft extending distally from the handle, and a torque limiting mechanism. In accordance with other embodiments of the seventh aspect, the torque limiting mechanism may be configured as described above in connection with the first aspect.

An eighth aspect of the present invention is a method of inserting an implant using a surgical instrument including introducing an anchor rod into a lumen of a body of the surgical instrument, the lumen extending from a proximal end to a distal end of the body along an axis, and advancing the anchor rod within the lumen until the anchor rod is connected to the body at the proximal end and at the distal end of the body to substantially fix the anchor rod from moving along the axis of the lumen.

In accordance with other embodiments of the eighth aspect, the step of advancing the anchor rod within the lumen may include advancing the anchor rod within the lumen until the anchor rod is connected to the body at the distal end of the body, and then advancing the anchor rod further within the lumen until the anchor rod is connected to the body at the proximal end of the body. The anchor rod may be connected to the body at the distal end by contacting a distal stop of the anchor rod with a distal stop of the body. The anchor rod may be connected to the body at the proximal end by contacting a proximal stop of the anchor rod with a proximal stop of the body. The step of advancing the anchor rod further within the lumen may include translating a longitudinal shaft of the anchor body with respect to a distal shaft of the anchor body to shorten the length of the anchor body. The step of advancing the anchor rod further within the lumen may include compressing the anchor body to shorten its length. The length of the anchor body may be shortened due to compression of an internal spring within the anchor body. The proximal stop of the body may be located on a movable toggle. The step of advancing the anchor rod further within the lumen may include temporarily moving the toggle to an unlocked position by contact with the anchor rod as the proximal stop of the anchor rod is moved distally past the proximal stop of the toggle. The toggle may be normally biased into a locked position in which the proximal stop of the anchor rod contacts the proximal stop of the body and cannot move proximally past the proximal stop of the body.

The method may further include assembling an implant to a distal end of a body of the surgical instrument by rotating a distal end of the anchor rod to contact the implant to secure the implant at the distal end of the body. The method may further include angling a distal end of the instrument and the attached implant with respect to a proximal end of the instrument through a joint in the body and a linkage in the anchor rod. The method may further include striking a proximal end of the instrument during insertion of the implant, wherein the substantial fixation of the anchor rod within the lumen substantially eliminates breakage or failure of the anchor rod. The implant may be inserted into an intervertebral disc space.

A ninth aspect of the present invention is a method of inserting an implant using a surgical instrument including introducing an anchor rod into a lumen of a body of the surgical instrument, the lumen extending from a proximal end to a distal end of the body along an axis, and assembling an implant to a distal end of a body of the surgical instrument by rotating a distal end of the anchor rod to contact the implant to secure the implant at the distal end of the body, wherein a maximum amount of torque that can be applied to the anchor rod during assembly of the implant is limited by a torque limiting mechanism of the instrument.

In accordance with other embodiments of the ninth aspect, the step of assembling the implant may include rotating a portion of the torque limiting mechanism about an axis of the torque limiting mechanism to transfer torque from the torque limiting mechanism to the anchor rod. Rotation of the torque limiting mechanism in a first direction about the axis of the torque limiting mechanism may cause rotation of the anchor rod up to a predetermined maximum torque value applied to the torque limiting mechanism, and rotation of the torque limiting mechanism in a second direction opposite the first direction about the axis of the torque limiting mechanism may always cause rotation of the anchor rod about the axis of the torque limiting mechanism. The step of assembling the implant may include rotating a portion of the torque limiting mechanism about an axis of the torque limiting mechanism until the maximum amount of torque is reached. The step of assembling the implant may include rotating a portion of the torque limiting mechanism about an axis of the torque limiting mechanism until the maximum amount of torque is exceeded. The method may further include angling a distal end of the instrument and the attached implant with respect to a proximal end of the instrument through a joint in the body and a linkage in the anchor rod. The method may further include striking a proximal end of the instrument during insertion of the implant, wherein the substantial fixation of the anchor rod within the lumen substantially eliminates breakage or failure of the anchor rod. The implant may be inserted into an intervertebral disc space.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

As shown in FIGS. 1-17, a first embodiment of a surgical instrument 100 is provided that allows for different angles to be created between its main axis and the axis of a corresponding surgical implant. Instrument 100 has a body including a handle 102 and a shaft 104 extending along an axis, and an anchor rod 106 that is disposed within the hollow construct of handle 102 and shaft 104 to secure a surgical implant to the distal end of shaft 104.

Figure 1:
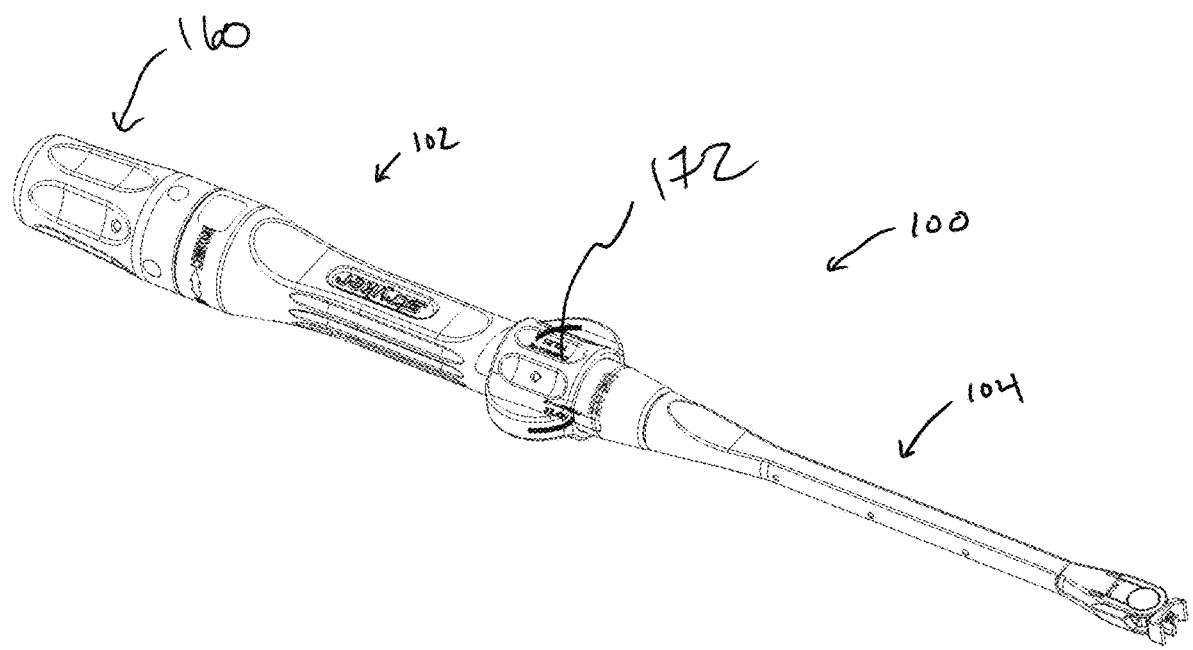
FIG. 1 is a perspective view of a surgical instrument in accordance with one embodiment of the present invention.
Figure 2:
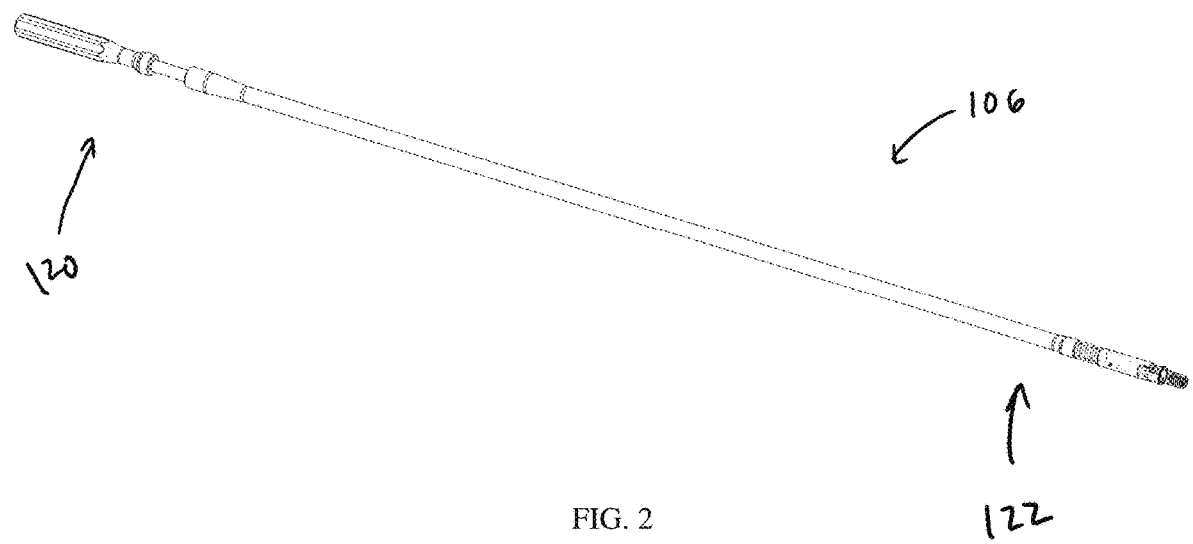
FIG. 2 is a perspective view of an anchor rod of the instrument shown in FIG. 1.
Figure 3:
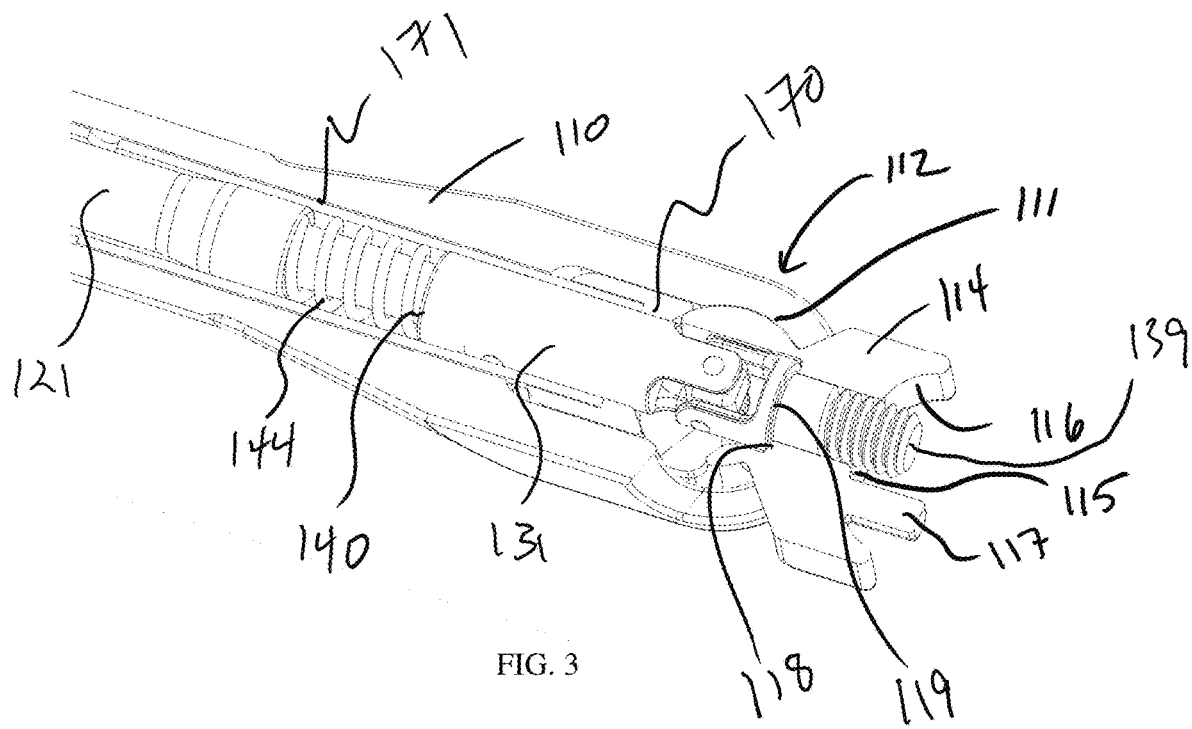
FIGS. 3 and 4 are perspective sectional views of a distal end of the instrument shown in FIG. 1.
Figure 4:
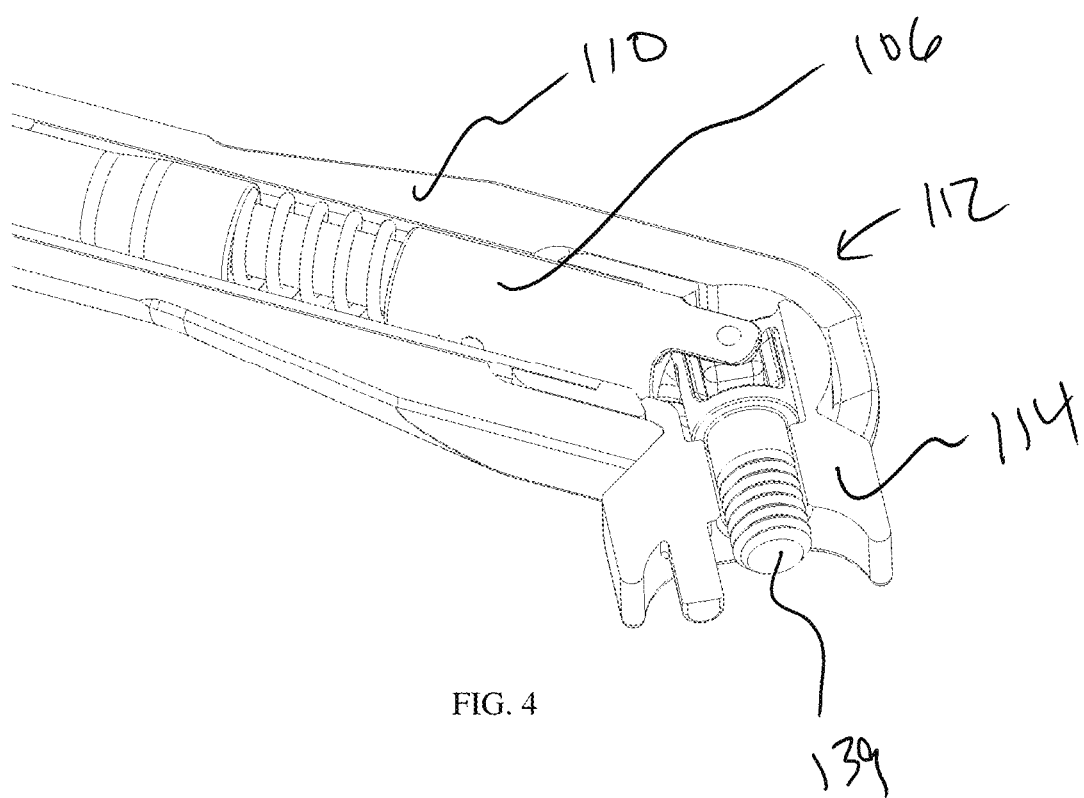
Figure 5:
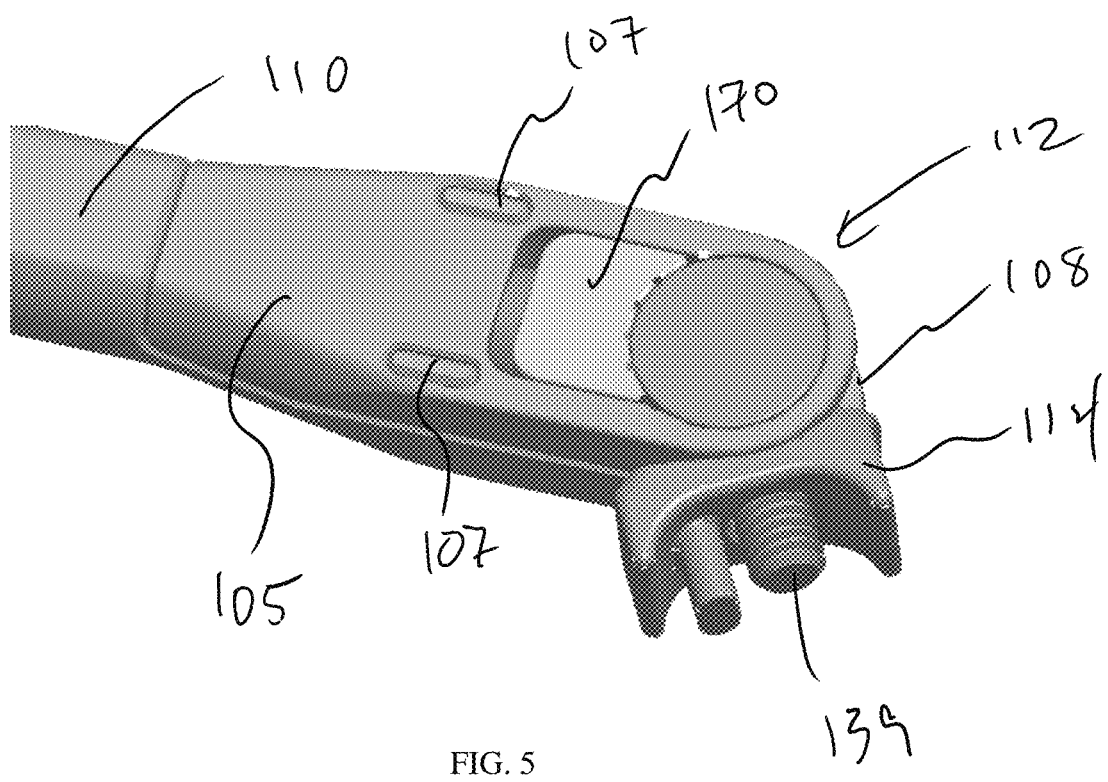
FIG. 5 is a perspective view of a distal end of the instrument shown in FIG. 1.
Figure 10:
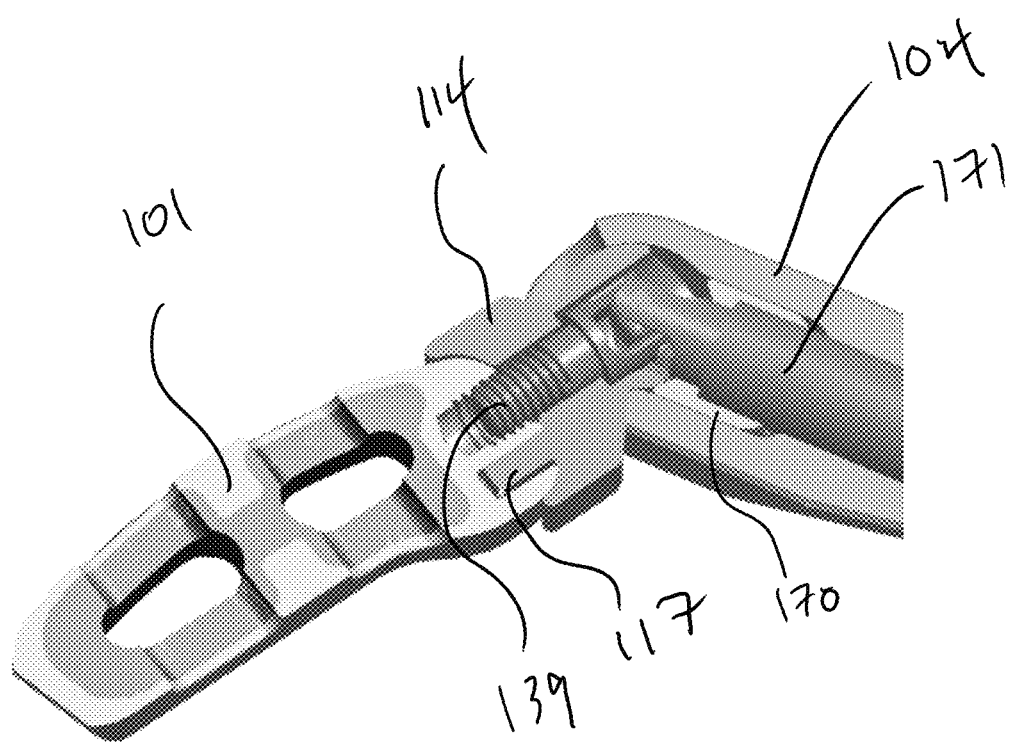
FIG. 10 is a perspective sectional view of a distal end of the instrument shown in FIG. 1 connected with an implant.
Figure 11:
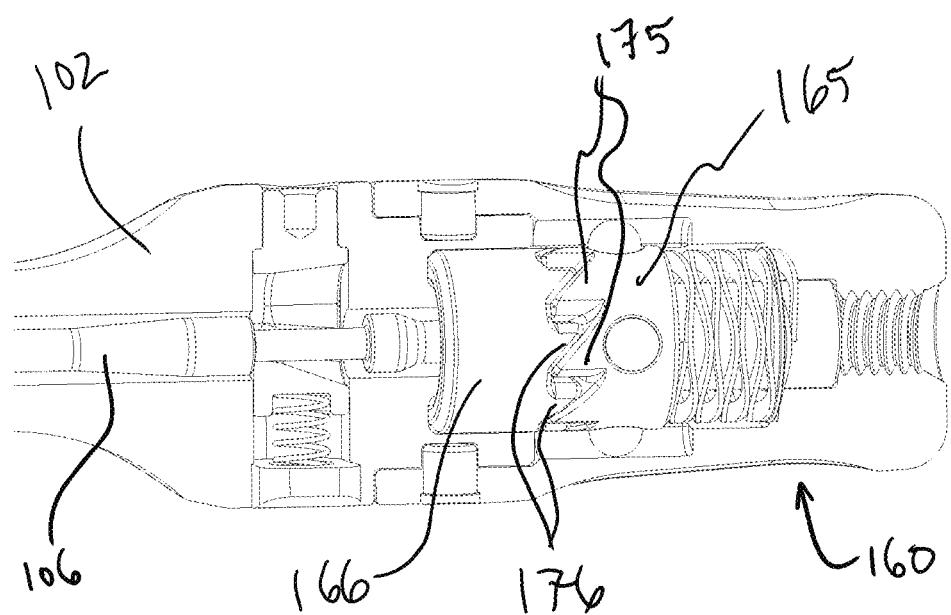
FIGS. 11 and 12 are perspective partial sectional views of a proximal end of the instrument shown in FIG. 1.
Figure 12:
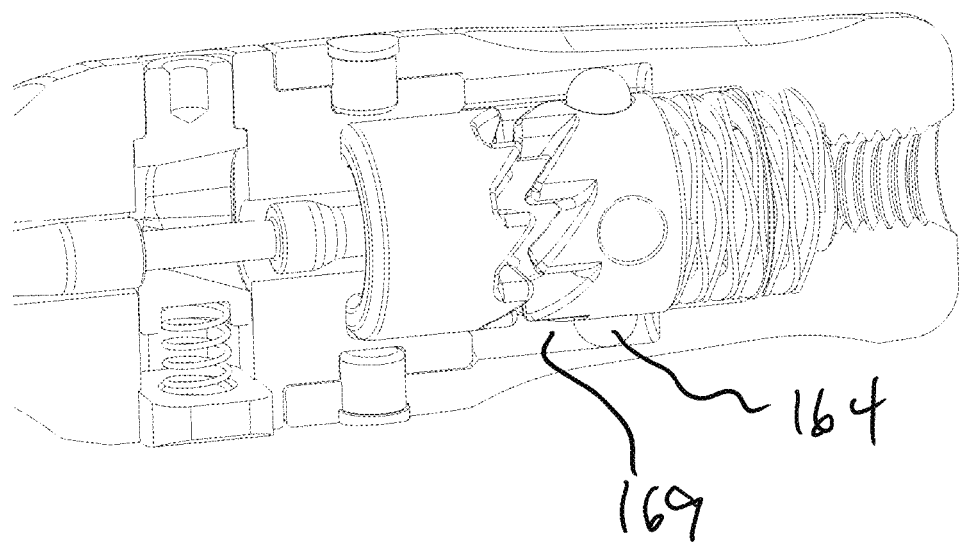
Figure 13:
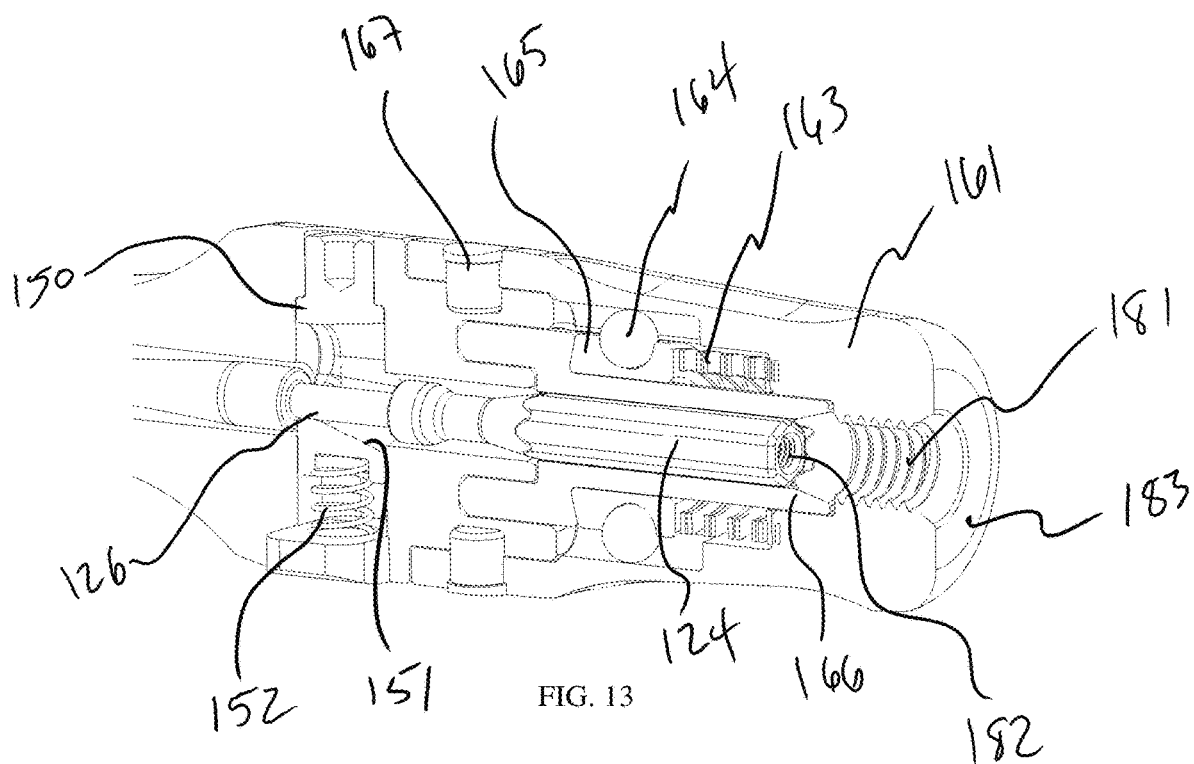
FIG. 13 is a perspective sectional view of a proximal end of the instrument shown in FIG. 1.
Figure 14:
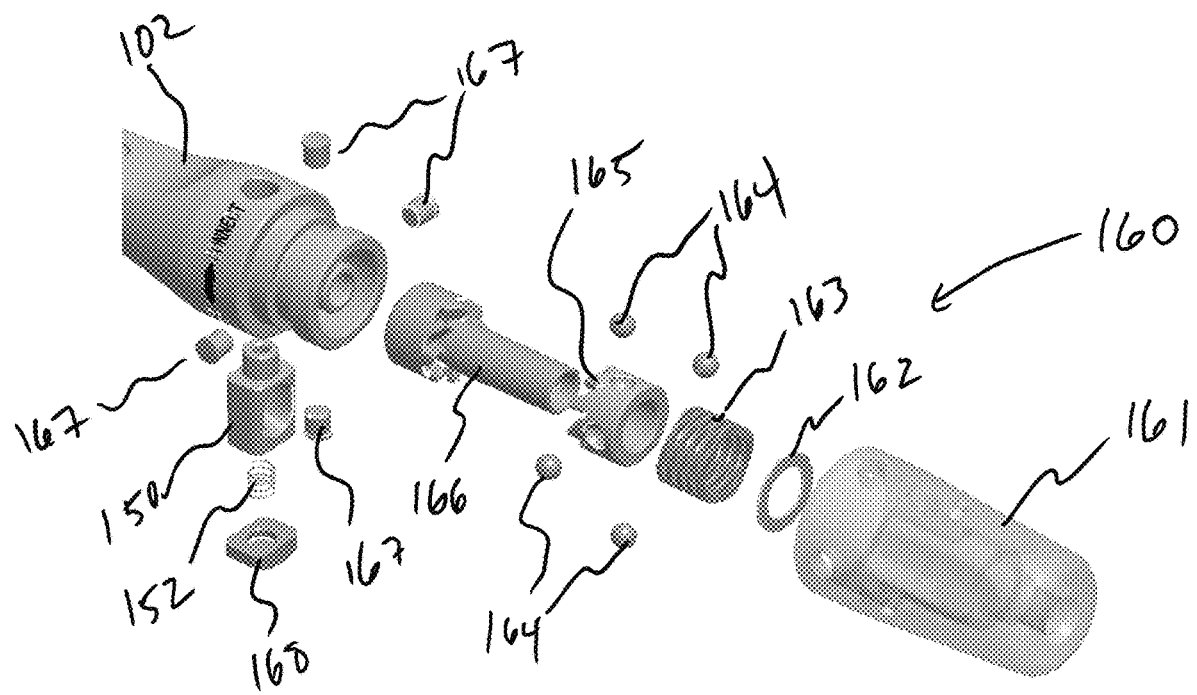
FIG. 14 is a perspective exploded view of a proximal end of the instrument shown in FIG. 1.
Figure 15:
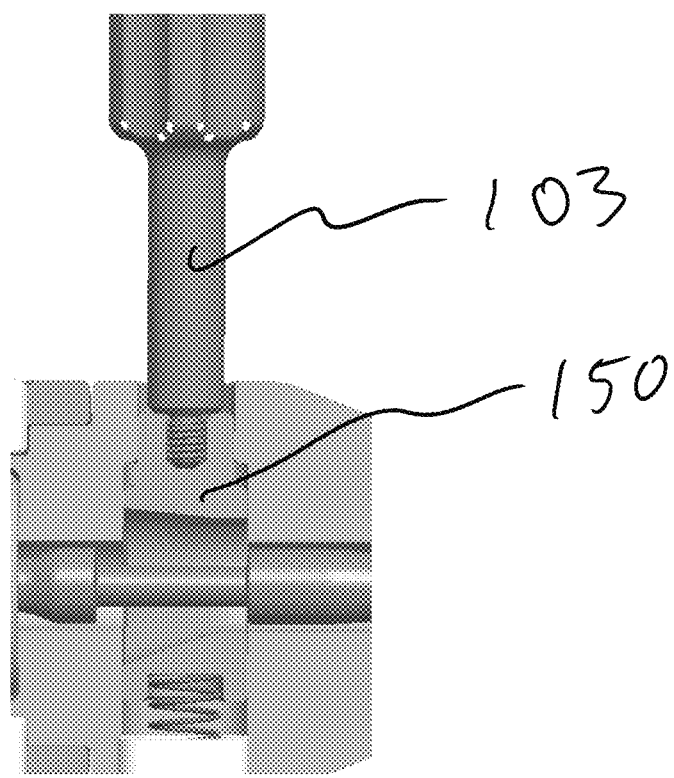
FIG. 15 is a perspective partial sectional view of toggle at a proximal end of the instrument shown in FIG. 1.
Figure 16:
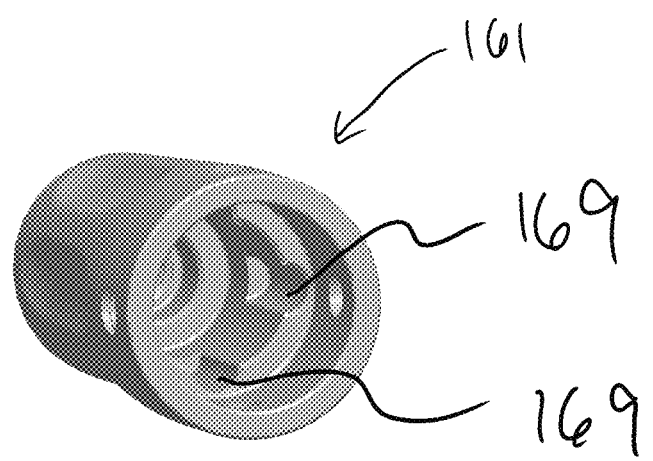
FIG. 16 is a perspective view of a rear knob of the instrument shown in FIG. 1.
Figure 17:
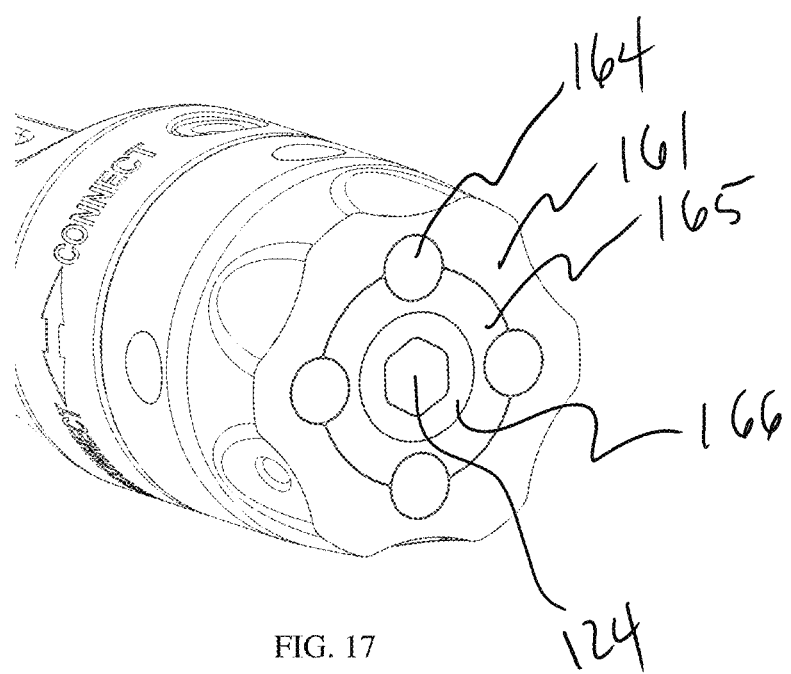
FIG. 17 is a perspective sectional view of a proximal end of the instrument shown in FIG. 1.

Shaft 104 has a main portion 110 connected at a joint 112 to a junction block 114 at a distal end of shaft 104, as depicted in FIGS. 3-5. Junction block 114 is partially seated within a recess 111 in main portion 110 so that it is pivotally connected with main portion 110 of shaft 104. A distal end of junction block 114 includes a face 116 from which a distal threaded rod 139 of anchor rod 106 protrudes through an aperture 115. Face 116 is curved to substantially match a curve of a corresponding implant 101, as shown in FIG. 10, so that the connection between same is flush during insertion. An anti-rotation feature 117 is also disposed on face 116 for connection with an implant to prevent relative rotation between the implant and instrument 100 when the two are connected. Both junction block 114 and main portion 110 of shaft 104 are hollow to define a lumen therethrough. When junction block 114 is pivoted at joint 112 with respect to main portion 110, the lumen of shaft 104 angles accordingly as shown in FIGS. 4, 5, and 10.

Figure 9:
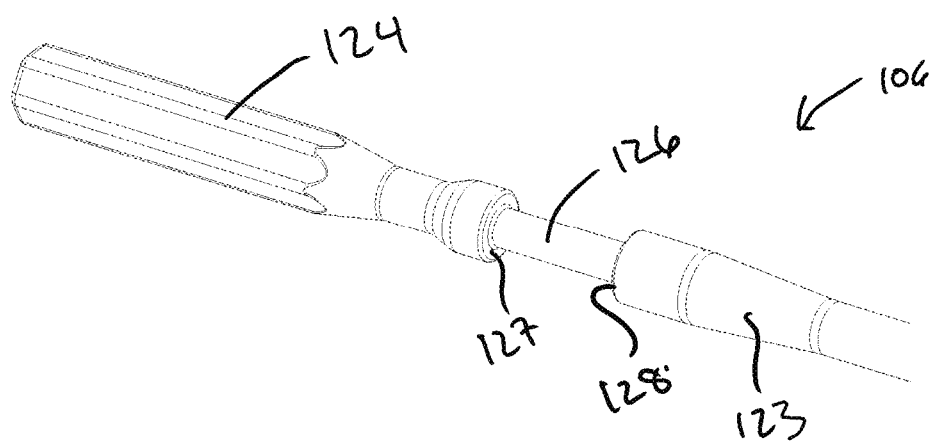
FIG. 9 is a perspective view of a proximal end of the anchor rod shown in FIG. 2.

Anchor rod 106 is a small diameter shaft used to thread and unthread spinal implant 101 to an articulating inserter such as the body of instrument 100. Anchor rod 106 has a long slender body having a proximal end 120 and a distal end 122 each engageable with different portions of handle 102 and shaft 104, respectively. As shown in FIG. 9, proximal end 120 has a shank 124 with a non-circular, in this case hexagonal, cross-section for mating with a similarly shaped lumen in handle 102. Distal of shank 124, a slim neck 126 is positioned between two portions of anchor rod 106 that are thicker in diameter. That is, neck 126 is located between two annular shoulders 127, 128. A conical portion 123 is disposed proximally of neck 126 that tapers from the larger diameter at shoulder 128 to a smaller diameter toward the midsection of anchor rod 106.

At distal end 112 of anchor rod 106, a linkage 129 is provided so that anchor rod 106 can both rotate within shaft 104 to secure an implant to instrument 100 and also articulate with joint 112 of shaft 104 to maintain engagement with the implant regardless of the configuration of joint 112. The shaft/tip of anchor rod 106 at distal end 112 is able to rotate 360 degrees about its axis while at any angle between 0 and 60 degrees with respect to the remainder of shaft 121, shown in FIGS. 3 and 4, respectively. That is, joint 112 and linkage 129 can each bend together to allow an angle to be made in instrument 100. Of course, larger or smaller maximum angles are possible depending on the size of the components and the intended use of instrument 100.

Figure 6:
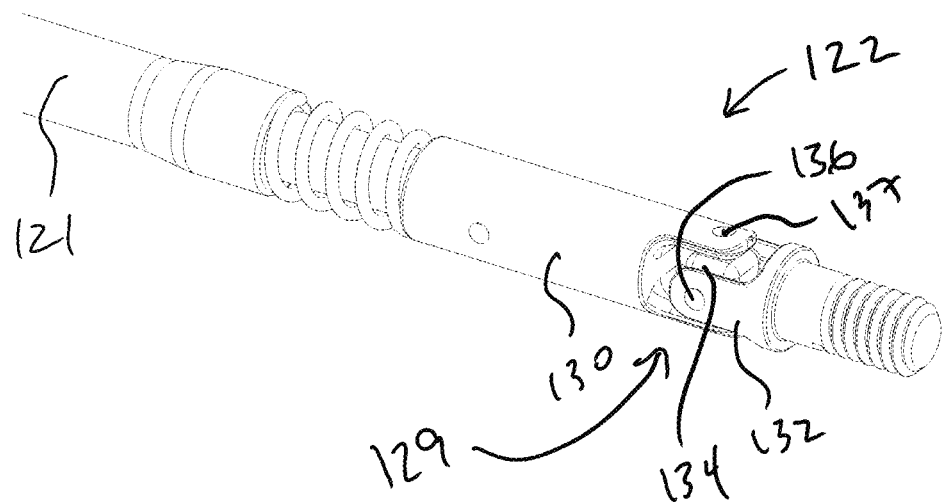
FIGS. 6 and 7 are perspective assembled and exploded views, respectively, of a distal end of the anchor rod shown in FIG. 2.
Figure 7:
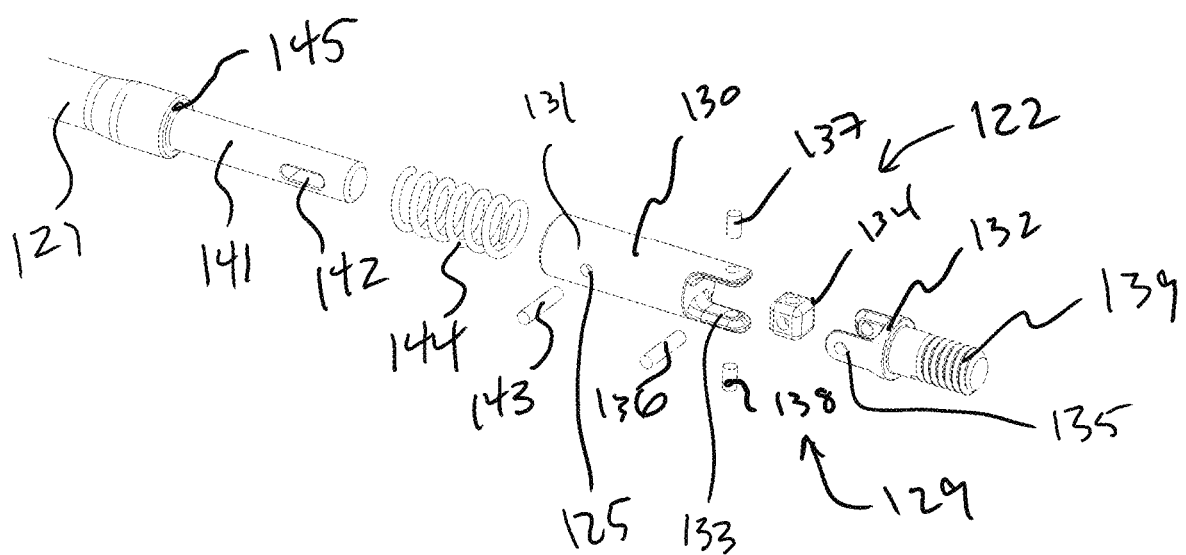
Figure 8:
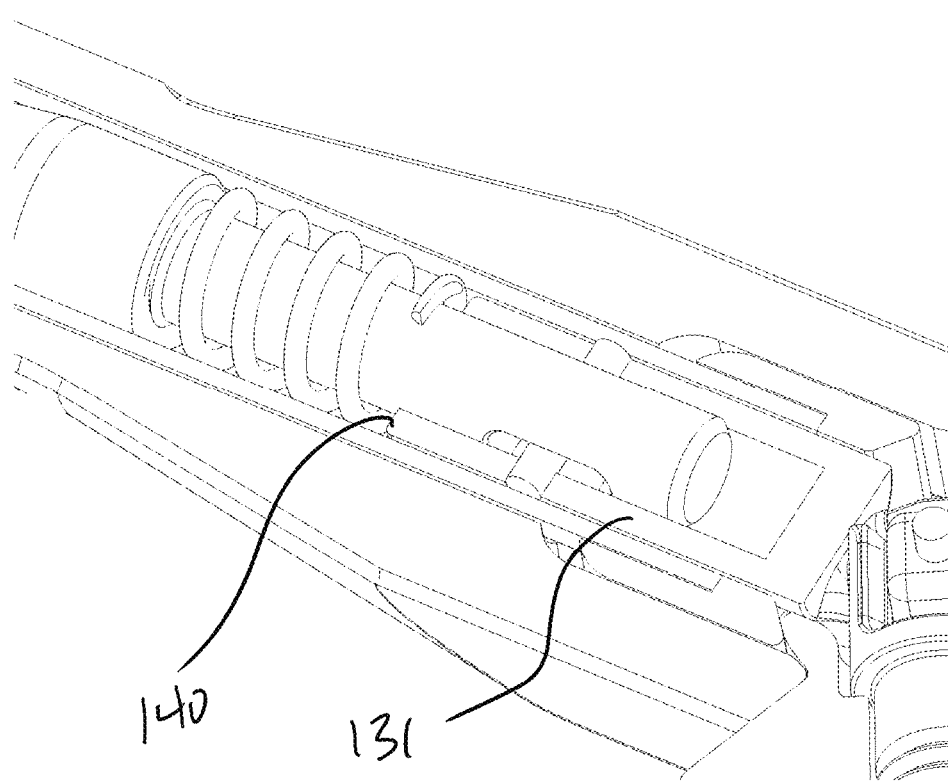
FIG. 8 is a perspective sectional view of a distal end of the instrument shown in FIG. 1.

The ability of anchor rod 106 to rotate and form angles is made possible by two U-joints 130 and 132, a pivoting block 134, and three pins 136, 137, and 138 located at the center of rotation of linkage 129, as shown in FIGS. 6 and 7. U-joint 130 has a hollow cylindrical proximal end 131 with a forked distal end 133 defining the U-shape. U-joint 132 has a similar proximally-facing forked end 135 and a distal threaded rod 139 for engaging the implant. Pivoting block 134 is disposed between both forked ends 133, 135 when U-joints 130 and 132 are aligned. In this configuration, in order for pins 136, 137, and 138 to be located on center, pin 136 is connected from ear to ear of forked end 135 as one solid connection on U-joint 132. Pins 137 and 138 are each individually connected to the ears of forked distal end 133 of U-joint 130. That is, pin 136 extends completely through pivoting block 134 and through apertures in each ear of forked end 135 of U-joint 132. Each of pins 137 and 138 extends partially through pivoting block 134 and through a respective aperture in one of the ears of forked distal end 133 of U-joint 130. All three pins 136, 137, and 138 pass through and into the center pivoting block 134 which is the area of transfer when anchor rod 106 is rotated and/or torqued. All three pins 136, 137, and 138 are free to move independently of one another, which allows the device to work properly. This construct keeps the pivoting area of anchor rod 106 within the same general outer diameter of the two shaft portions of U-joints 130 and 132 when angled, which prevents any binding or roll over while being captured in a small concealed area. This allows for the pivot area/block to rotate 360 degrees within the same diameter of the two shafts 130, 132.

Figure 18A:
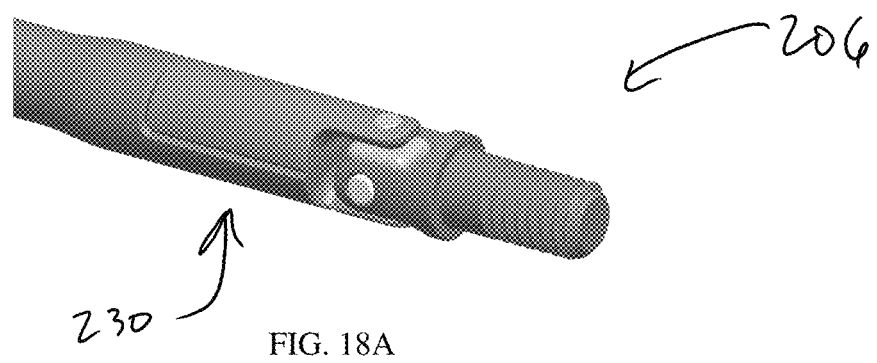
FIGS. 18A and 18B are perspective assembled and exploded views, respectively, of a distal end of an anchor rod for a surgical instrument in accordance with another embodiment of the present invention.
Figure 18B:
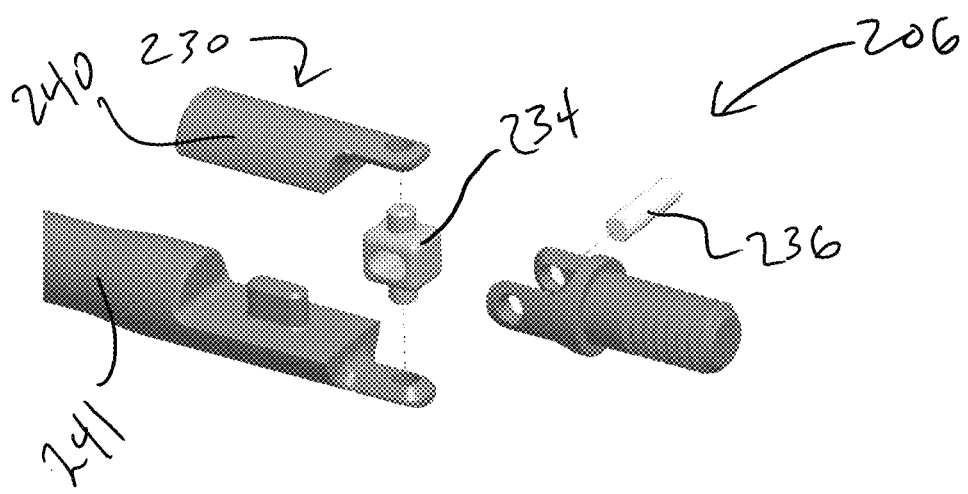

In an alternate embodiment, an anchor rod 206 is shown in FIGS. 18A and 18B. Anchor rod 206 includes a monolithic pivoting block 234 having its own pins extending out from opposite ends. Pivoting block 234 is then capped by the second half 240 of the shaft to the longitudinal shaft 241, which together comprise U-Joint 230, capturing and securing pivoting block 234. There is an anti-rotation feature built in to provide extra strength. The two halves of U-joint 230 are then welded as one part. Otherwise, anchor rod 206 works similarly to anchor rod 106. Pins 236 passes through a hole in pivoting block 234 and have a very close slip fit allowing the pins of pivoting block 234 to move freely when turned.

Figure 19A:
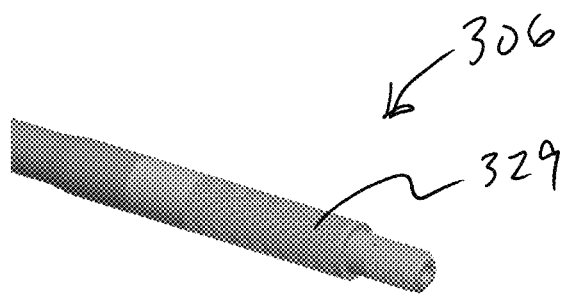
FIGS. 19A and 19B are perspective and side sectional views, respectively, of a distal end of an anchor rod for a surgical instrument in accordance with another embodiment of the present invention.
Figure 19B:
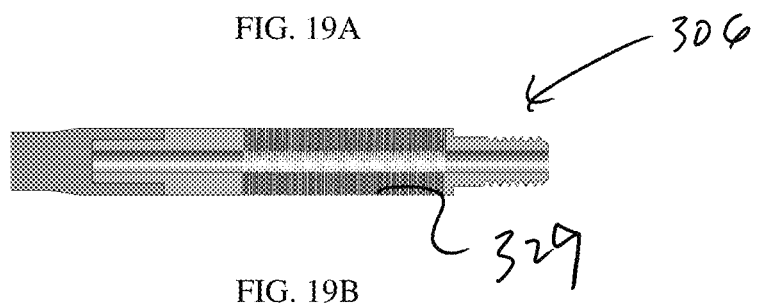

In a further alternative embodiment, an anchor rod 306 is shown in FIGS. 19A and 19B having a machined spring 329 at the distal end of the shaft. Spring 329 allows anchor rod 306 to transmit torque while being flexible about the angled orientations that shaft 104 can assume.

Further concerning instrument 100, a longitudinal shaft 121 of anchor rod 106 is provided proximal of the linkage 129. Longitudinal shaft 121 has a distal end portion 141 of a smaller diameter than the main portion of longitudinal shaft 121 and that is slidably disposed within hollow cylindrical proximal end 131 of U-joint 130. A slot 142 is defined within distal end portion 141 of longitudinal shaft 121 that is aligned with opposing apertures 125 in cylindrical proximal end 131 of U-joint 130. A pin 143 is disposed in slot 142 and the opposing apertures 125 of U-joint 130 to connect longitudinal shaft 121 to U-joint 130 while allowing some respective movement between longitudinal shaft 121 and U-joint 130 along the aligned axes of both, as allowed by the length dimension of slot 142.

A spring 144 is positioned about distal end portion 141 of longitudinal shaft 121 and is contacted at one end by a shoulder 145 of longitudinal shaft 121 and at the other end by a proximal face 140 of cylindrical proximal end 131 of U-joint 130. Thus, at rest, spring 144 forces longitudinal shaft 121 and U-joint 130 apart from one another until pin 143 contacts the distal most end of slot 142. When compressed, spring 144 allows movement of longitudinal shaft 121 relative to U-joint 130 until pin 143 contacts the proximal most end of slot 142. This configuration allows the anchor rod 106 to compress in length when inserted into the lumen of shaft 104.

As anchor rod 106 is inserted into instrument 100, neck 126 is moved into communication with a toggle 150 within handle 102, as shown in FIGS. 11-15. Toggle 150 is displaceable vertically within handle, i.e. in a direction perpendicular to the axis of handle 102 and shaft 104. Toggle 150 defines a lumen that is aligned with the lumens of handle 102 and shaft 104 so that instrument 100 as a whole is cannulated from end to end. The lumen of toggle 150 has a conically shaped inner surface 151 with a smaller aperture at the distal end. As anchor rod 106 is moved distally, conical portion 123 contacts conically shaped inner surface 151 of the lumen of toggle 150 to temporarily bias toggle 150 in a downward position against the force of a spring 152 that tends to force toggle 150 upward. Once shoulder 128 of anchor rod 106 clears the smaller aperture at the distal end of toggle 150 in a distal direction, spring 152 forces toggle 150 upward so that the smaller aperture contacts neck 126 and shoulder 128. This prevents anchor rod 106 from being able to move proximally out of instrument 100. The configuration of conically shaped inner surface 151 also allows anchor rod 106 to be inserted without having to press toggle 150 downward to initiate the capture feature. A plug 168 is disposed beneath toggle 150 and captures the other end of spring 152.

Instrument 100 is calibrated so that as this occurs, spring 144 at distal end 122 of anchor rod 106 is compressed as the smaller diameter distal end portion 141 of longitudinal shaft 121 moves further into hollow cylindrical proximal end 131 of U-joint 130. That is, as anchor rod 106 is moved into shaft 104, a shoulder 119 of U-joint 132 hits an internal wall 118 of junction block 114, which defines the furthest position that U-joint 132 can be moved distally within shaft 104. When this contact initially occurs, neck 126 is not yet fully seated within toggle 150. Further movement of longitudinal shaft 121 of anchor rod 106 requires at least some compression of spring 144 to fully seat neck 126 within toggle 150.

Anchor rod 106 then decompresses when released, which creates a fully captured anchor rod 106 with no toggle or movement within the body of instrument 100. That is, anchor rod is pinned from both ends to substantially lock its position with respect to the body of instrument 100.

The back capture feature of toggle 150 contains and captures the entire anchor rod 106 within instrument 100. This allows anchor rod 106 to operate as one with the external instrument, i.e. handle 102 and shaft 104, during impaction. It has been found that a positive impaction force in one direction creates negative force in the opposite direction. This can put an extreme push/pull reaction to the pivoting area and pins, which can result in failure to several parts. By capturing the entire anchor rod 106 and keeping it contained, failure of anchor rod 106 and stress to the pins/parts at the tip of anchor rod 106 are significantly reduced or eliminated. In this regard, the spring 144 and slot 142 operate like a piston. When anchor rod 106 is inserted, spring 144 allows for the longitudinal shaft 121 to be compressed past the containment/flat/button feature of toggle 150. Once the shaft shoulder 128 is inserted past toggle 150, toggle 150 will spring back to capture shoulder 128 at the proximal end of anchor rod 106. As the user releases forward pressure and allows anchor rod 106 to spring back, it will then become fully captured within instrument 100. This also gives the design plenty of room for tolerance stack-up so that it still remains movement free.

Together, the proximally-facing force applied by junction block 114 on U-joint 132 and the opposing distally facing force applied by toggle 150 on shoulder 128 secure anchor rod 106 within the lumen of shaft 104 so that it is firmly seated and does not substantially move during use of instrument 100. Spring 144 can be designed with a particular stiffness to dictate how firmly or loosely these forces act on anchor rod 106. Instrument 100 can be calibrated so that anchor rod 106 can withstand movement within shaft 104 when handle 102 is impacted at its proximal end to assist in seating an implant during insertion.

To remove anchor rod 106 after use, an internal insertion tool 103 is threaded into an upper aperture in toggle 150. The user then holds the distal end of instrument 100 upward while using insertion tool 103 to press toggle 150 into handle 102 in a downward direction along the axis of toggle 150. This allows toggle 150 to disengage from anchor rod 106 so that it can release and drop out freely. In order to disengage anchor rod 106, its entire length should be aligned along one axis so that there is no interference at joint 112. In other embodiments, toggle 150 can be depressed manually without a separate tool.

When anchor rod 106 is disposed within the body of instrument 100, the angle of junction block 114 with respect to shaft can be maintained via clamp 170 that presses against the proximal end of junction block 114, as shown in FIG. 5. The distal face of clamp 170 can be curved to match the curvature of the proximal end of junction block 114 so that a tight friction fit is created. In other embodiments, the mating surfaces may each be a plurality of planar faces that can be mated when aligned at multiple orientations. Clamp 170 is attached to a hollow rod 171 that extends proximally to a collar 172 on the exterior of the body of instrument 100. Rotation of collar 172 translates hollow rod 171 to lock or unlock clamp 170 from junction block 114, accordingly. This enables the relative angle at the distal end of instrument to be locked in place during a portion of the procedure.

Once the components at the distal end of shaft 104 are assembled, a top half 105 of the shaft 104 is assembled onto the main portion of shaft 104 by aligning it with two posts 107, as shown in FIG. 5. Together, the main portion of shaft 104 and top half 105 of shaft 104 create a distally facing window 108 through which a distal portion of junction block 114 extends through the various angles.

As shown in FIGS. 11-14, a torque limiting mechanism 160 is located at the proximal end of handle 102. This allows the user to attach an implant 101 to the distal end of shaft 104 while threading down anchor rod 106 creating a secure connection without over torqueing or damaging either implant 101 or instrument 100. The required torque is predetermined and calculations are done to develop the correct gears (friction, teeth, pitch and diameters), spring, and required spring force, as well as all the housing and drive mechanisms, to all work within the allowable size requirements of instrument 100.

The design includes two opposing gears, a proximal torque gear 165 and a distal torque gear 166, and the use of ball bearings 164 which allow full engagement to handle 102 while allowing the actuation needed for one gear to slide back and forth so that both gears 165, 166 can disengage easily from one another. By having the torque limiting feature added to instrument 100, the amount of steps needed by the user to thread and unthread anchor rod 106 to implant 101 in surgery will be reduced. It will also eliminate the need to purchase or use an expensive standalone torque limiting driver as part of the necessary instrument set, allowing more room in the surgical tray and one less item to invoice as a referenced part.

Rear knob 161 has an external gripping surface and an internal cavity that houses other components of torque limiting mechanism 160. A torque spacer 162 is seated within the cavity of rear knob 161 and against a wave spring 163, which exerts force between torque spacer 162 and proximal torque gear 165. Proximal torque gear 165 includes distally facing teeth 175 that engage proximally facing teeth 176 of distal torque gear 166. Distal torque gear 166 also has a hollow cylindrical shaft extending proximally from within its teeth 176, such that torque spacer 162, wave spring 163, and proximal torque gear 165 are all disposed about the hollow cylindrical shaft of distal torque gear 166.

In a rear end of rear knob 161, a threaded recess 181 is provided in which external tools can be secured. For instance, a slap hammer can be anchored directly to instrument 100 via threaded recess 181 to assist in removing or inserting an implant during a surgical procedure in which instrument 100 is used. The proximally facing surface 183 of rear knob 161 also serves as an impact surface that can be stricken with a mallet to assist during insertion of an implant. Proximal end of 120 of anchor rod 106 also includes a threaded recess 182 in which an instrument can be connected to aid in inserting and/or removing anchor rod 106 from its position within instrument 100.

As shown in FIGS. 11-14 and 17, four ball bearings 164 are positioned in hemispherical recesses on the exterior surface of proximal torque gear 165. The inner surface of rear knob 161 includes four axially extending hemicylindrical channels 169 in which ball bearings 164 are received. Because the external diameter of proximal torque gear 165 and the inner diameter of rear knob 161 are substantially similar, rear knob 161 is rotationally locked with respect to proximal torque gear 165 since ball bearings cannot move circumferentially about the inner diameter of rear knob 161 or about the external diameter of proximal torque gear 165, as shown in the sectional view of FIG. 17. The longitudinal configuration of hemicylindrical channels 169 does allow for axial movement of proximal torque gear 165 with respect to rear knob 161. This axial movement is what allows torque limiting mechanism 160 to perform as intended.

Distal torque gear 166 is seated in an annular recess of the proximal end of handle 102, and rear knob 161 covers all of these elements of torque limiting mechanism 160 by slipping over the proximal end of handle 102 and being rotationally connected to handle 102 via four pins 167 that engage another annular groove in handle 102.

Attaching implant 101 to anchor rod 106 is done by turning/threading a rear knob 161 in a clockwise direction, which in turn rotates anchor rod 106 due to non-circular shank 124 of anchor rod 106 being mated with a similarly shaped lumen in handle 102. When rear knob 161 is rotated, its rotational movement is translated to rotational movement of proximal torque gear 165 via ball bearings 164. This rotational movement is also translated to rotational movement of distal torque gear 166 since wave spring 163 tends to maintain contact between proximal and distal torque gears 165, 166. The teeth of each of proximal and distal torque gear 165, 166 are each configured to have one face that is axially aligned with the central axis of each gear 165, 166, and another face that is angled with respect to the central axis of each gear 165, 166. When rear knob 161 is rotated clockwise, this places pressure and friction on the angled faces of each pair of teeth. Instrument 100 is calibrated to balance the tensile force in spring 163 against the pressure and friction forces on angled faces of teeth when gears 165, 166 are joined. When rear knob is rotated 161 clockwise, the pressure and friction on the angled faces of each pair of teeth allow the clockwise rotation of proximal torque gear 165 to translate into clockwise rotation of distal torque gear 166. This in turn rotates anchor rod 106 via the non-circular connection to draw the implant against the distal end of instrument 100 until it is fully seated.

Once anchor rod 106 is fully threaded into the implant and the allowable torque is reached (i.e. when the implant is seated), wave spring 163 will begin to depress and allow for the two opposing gears 165, 166 to disengage. This then prevents any further turning to anchor rod 106 connected to the implant. If the user is to continue turning rear knob 161 the entire mechanism will continue to slip/disengage with an audible clicking sound, thus preventing damage. That is, the force needed to turn anchor rod 106 is at this point increased to a value greater than the friction forces on the angled faces of teeth, which allows the teeth and gears 165, 166 to separate axially, which in turn compresses spring 163. As proximal torque gear 165 moves proximally, ball bearings 164 move proximally in hemicylindrical channels 169 until teeth are able to slip past one another. That is, when the two opposing gears 165, 166 turn and begin to separate ball bearings 164 allow for gears 165, 166 to slide linear/back and forth and turn 360 degrees at the same time. Spring 163 then pushes the teeth back together, though the same magnitude of rotational force on knob 161 will again cause teeth to slip past one another while the maximum torque value is exceeded. The calibration of instrument 100, including the angle of the teeth faces and the tension in spring 163, results in a maximum torque being reached beyond which clockwise rotation of rear knob 161 will not further rotate anchor rod 106.

When unthreading anchor rod 106 from the implant, the design allows for an unlimited torque value to be achieved while rotating rear knob 161 counter clockwise. This is achieved due to the design of the flat on flat shoulders of proximal and distal torque gears 165, 166, allowing the user to disconnect instrument 100 from the implant. That is, the axially aligned faces of the teeth of each gear 165, 166 are parallel to one another, meaning that there will be no slippage when rear knob 161 is rotated counter clockwise. In this way, anchor rod 106 can always be turned to remove the implant from the distal end of instrument 100 because the force of spring 163 maintains the connection of gears 165, 166 when rear knob 161 is moved in a counter clockwise direction.

Most, if not all, torque limiting tools designed to connect with an implant are directly attached to the drive shaft in the instrument. In the present instrument, this is not the case. The torque limiting aspect of the present instrument is modular in that it allows for anchor rod 106 to be removed for cleaning and/or replacement as needed without disturbing the torque limiting mechanism. The present instrument allows for anchor rod 106 to be loosened or tightened while it is threaded at the far tip to the implant. If separation of the gears 165, 166 in the handle does not give gears 165, 166 the freedom to rotate and actuate back and forth at the same time, anchor rod 106 would then want to travel linearly, thus pushing itself forward and binding the entire system. Ball bearings 164 facilitate a more secure operation of the instrument by preventing such separation between the implant and the distal end of the shaft when the torque limit is reached. Ball bearings 164 are the engaging feature of the handle. Proximal torque gear 165 drives distal torque gear 166, which then drives anchor rod 106. Ball bearings 164 disposed in the four hemicylindrical channels 169 in rear knob 161 and the four hemispherical recesses in proximal torque gear 165 allow gears 165, 166 to rotate 360 degrees and to move linearly at once.

The instruments and the components thereof disclosed herein can be made of any rigid biocompatible materials or combinations thereof, such as a plastic, PEEK, Radel, Silastic and any various grades of stainless steel for medical application. Other similar metal materials are contemplated. Surgical materials that can be autoclaved for reuse can be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical instrument comprising:
    a body having a proximal end and a distal end and defining a lumen extending from the proximal end to the distal end along an axis, the distal end configured to abut an implant; and
    an anchor rod disposable within the lumen of the body for contacting the implant to secure the implant at the distal end of the body,
    wherein when the anchor rod is disposed within the lumen of the body in a working configuration, the anchor rod is connected to the body at the proximal end of the body and at the distal end of the body to substantially fix the anchor rod from moving along the axis of the lumen,
    wherein when the anchor rod is in the working configuration, the anchor rod is connected to the body at the proximal end by a proximally-facing surface of the anchor rod in contact with a distally-facing surface of the body,
    wherein the distally-facing surface of the body is located on a movable toggle, and
    wherein the toggle can be located in an unlocked position in which the proximally-facing surface of the anchor rod can move distally past the distally-facing surface of the toggle, and in a locked position in which the proximally-facing surface of the anchor rod contacts the distally-facing surface of the toggle and cannot move proximally past the distally-facing surface of the toggle.

2. The surgical instrument of claim 1, wherein the toggle is biased into the locked position.

3. The surgical instrument of claim 2, wherein the toggle is biased by a spring.

4. The surgical instrument of claim 2, wherein the toggle is temporarily moved to the unlocked position by contact with the anchor rod as the proximally-facing surface of the anchor rod is moved distally past the proximally-facing surface of the toggle.

5. The surgical instrument of claim 1, wherein when the anchor rod is in the working configuration, the anchor rod is connected to the body at the distal end by a distally-facing surface of the anchor rod in contact with a proximally-facing surface of the body.

6. The surgical instrument of claim 1, wherein the anchor rod is comprised of a longitudinal shaft and a distal shaft that are translatable relative to one another along an axis of the anchor rod.

7. The surgical instrument of claim 6, wherein the longitudinal shaft and the distal shaft are biased to move away from one another by an anchor body spring.

8. The surgical instrument of claim 7, wherein when the anchor rod is in the working configuration, the anchor body spring is at least partially compressed to exert force by the proximally-facing surface of the anchor rod on the distally-facing surface of the body and by a distally-facing surface of the anchor rod on a proximally-facing surface of the body.

9. The surgical instrument of claim 1, wherein the body defines a joint permitting the distal end to articulate relative to the proximal end.

10. The surgical instrument of claim 9, wherein the anchor rod has a linkage connecting proximal and distal ends thereof, wherein the body and the anchor rod can articulate together when the anchor rod is disposed within the body and the joint and the linkage are aligned.

11. A kit comprising:
    the surgical instrument of claim 1; and
    a spinal implant.

12. The surgical instrument of claim 1, wherein the body comprises a handle, a shaft extending distally from the handle, and a torque limiting mechanism.

13. The surgical instrument of claim 12, wherein the torque limiting mechanism includes a first gear mechanism defining a lumen in which a portion of the anchor rod is disposed when the anchor rod is in the working configuration, and a second gear mechanism connected to the first gear mechanism.

14. The surgical instrument of claim 13, wherein the lumen of the first gear mechanism has a non-circular cross section substantially matching a noncircular cross section of the portion of the anchor rod so that rotational forces of the first gear mechanism are transferred to rotational forces of the anchor rod.

15. The surgical instrument of claim 13, wherein rotation of the second gear mechanism in a first direction about the axis of the torque limiting mechanism causes rotation of the first gear mechanism about the axis of the torque limiting mechanism up to a predetermined maximum torque value applied to the second gear mechanism, and rotation of the second gear mechanism in a second direction opposite the first direction about the axis of the torque limiting mechanism always causes rotation of the first gear mechanism about the axis of the torque limiting mechanism.

16. The surgical instrument of claim 15, wherein the first and second gear mechanisms each have teeth that provide an interface, the interfaces engaging with one another to facilitate the transfer of torque from one of the first and second gear mechanisms to the other, and wherein the teeth of each of the first and second gear mechanisms are each defined by a first tooth surface substantially parallel with the axis of the torque limiting mechanism and a second tooth surface angled with respect to the axis of the torque limiting mechanism.

17. A surgical instrument comprising:
 a body having a proximal end and a distal end and defining a lumen extending from the proximal end to the distal end along an axis, the distal end configured to abut an implant; and
 an anchor rod disposable within the lumen of the body for contacting the implant to secure the implant at the distal end of the body,
 wherein when the anchor rod is disposed within the lumen of the body in a working configuration, the anchor rod is connected to the body at the proximal end of the body and at the distal end of the body to substantially fix the anchor rod from moving along the axis of the lumen,
 wherein the anchor rod is comprised of a longitudinal shaft and a distal shaft that are translatable relative to one another along an axis of the anchor rod,
 wherein the longitudinal shaft and the distal shaft are biased to move away from one another by an anchor body spring, and
 wherein when the anchor rod is in the working configuration, the anchor body spring is at least partially compressed to exert force by a proximally-facing surface of the anchor rod on a distally-facing surface of the body and by a distally-facing surface of the anchor rod on a proximally-facing surface of the body.

18. The surgical instrument of claim 17, wherein the body defines a joint permitting the distal end to articulate relative to the proximal end.

19. A kit comprising:
 the surgical instrument of claim 17; and
 a spinal implant.

20. The surgical instrument of claim 17, wherein the body comprises a handle, a shaft extending distally from the handle, and a torque limiting mechanism.

* * * * *